US00PP30882P3

(12) United States Plant Patent
Kunieda

(10) Patent No.: US PP30,882 P3
(45) Date of Patent: Sep. 17, 2019

(54) ***ROSA* L. VARIETY NAMED '80102WABARA'**

(50) Latin Name: ***Rosa* L.**
Varietal Denomination: 80102WABARA

(71) Applicant: Rose Universe Co., Ltd., Shiga (JP)

(72) Inventor: Keiji Kunieda, Shiga (JP)

(73) Assignee: ROSE UNIVERSE CO., LTD., Shiga (JP)

( * ) Notice: Subject to any disclaimer, the term of this patent is extended or adjusted under 35 U.S.C. 154(b) by 0 days.

(21) Appl. No.: 15/932,566

(22) Filed: Mar. 15, 2018

(65) Prior Publication Data

US 2019/0239403 P1 Aug. 1, 2019

(30) Foreign Application Priority Data

Jan. 26, 2018 (JP) ..... PVP 32808

(51) Int. Cl.
*A01H 5/02* (2018.01)
*A01H 6/74* (2018.01)

(52) U.S. Cl.
USPC ..... Plt./108

(58) Field of Classification Search
USPC ..... Plt./108
See application file for complete search history.

*Primary Examiner* — Annette H Para
(74) *Attorney, Agent, or Firm* — Kilpatrick Townsend & Stockton LLP

(57) ABSTRACT

Described herein is a new and distinct rose variety named '80102WABARA'.

4 Drawing Sheets

Figure 1:
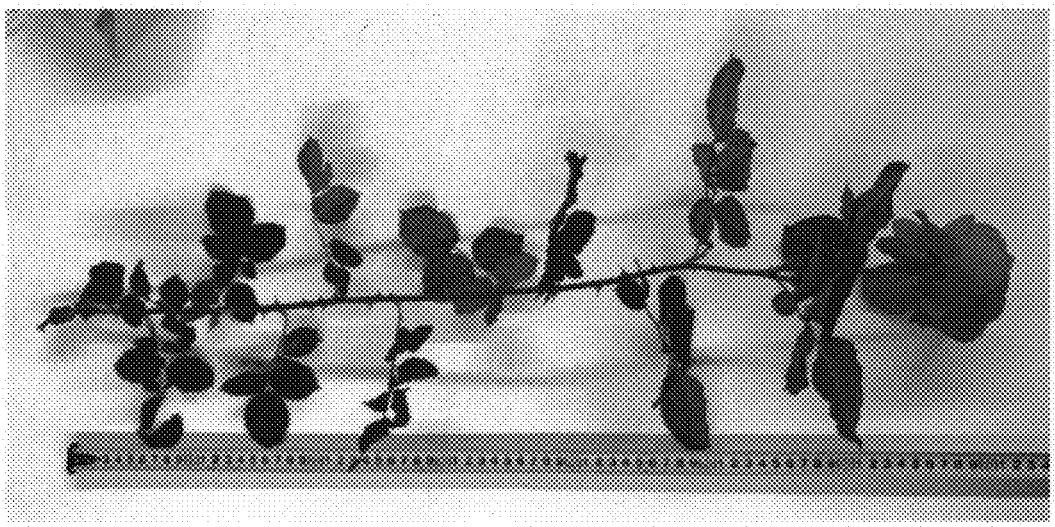

Genus and species: The rose variety of this invention is botanically identified as *Rosa* L.

Variety denomination: The variety denomination is '80102WABARA'.

CROSS-REFERENCES TO RELATED APPLICATIONS

This application claims priority to Japanese Plant Variety Protection Application No. 32808, filed Jan. 26, 2018.

BACKGROUND OF THE INVENTION

The present invention is a new and distinct variety of a *Rosa* L. rose plant obtained from a cross between maternal variety 'Misaki' and an unnamed paternal variety of unknown parentage owned by the breeder. The cross was performed by hand pollination in May 2014 and seeds were planted in January 2015. '80102WABARA' was selected from the varieties that flowered in September 2017. Stable characteristics were confirmed following selection.

BRIEF SUMMARY OF THE INVENTION

'80102WABARA' is reproduced by grafting. '80102WABARA' can be distinguished from a similar variety, 'Yuzen', by: (1) a large number of petals (115 petals compared to 58 for 'Yuzen'); (2) color grouping (red compared to peach for 'Yuzen'); (3) petal shape (changes from elliptic to fan-shaped from the center part to the outside compared to obovate for 'Yuzen'); (4) main color of the inner side of the petal (darker than RHS N57A compared to RHS 67B for 'Yuzen'); and (5) petal secondary color (RHS N66 compared to absent for 'Yuzen'). '80102WABARA' is also distinguished from comparison variety 'Keiji1002' by the main color of the inner side of the petal (darker than RHS N57A compared to RHS N57C for 'Keiji1002'); and flower fragrance (strong compared to medium for 'Keiji1002').

'80102WABARA' is distinguished from its female parent by flower color, flower shape and fragrance. The female parent flower color is RHS 62D (outer side) and RHS 65D (inner side). The female parent flower shape is rosette, whereas '80102WABARA' is flattened convex, and the female parent has a Damask modern fragrance compared to '80102WABARA', which has a stronger fragrance.

'80102WABARA' is distinguished from its male parent by flower color, branch thickness, and growth habit. The male parent flower color is RHS 79A. The growth habit is strongly spreading, whereas '80102WABARA' is semi-upright. The branch thickness is about 0.3 cm.

The variety '80102WABARA' has been asexually reproduced at 507-2, Kanegamoricho, Moriyama-shi, Shiga, 524-0045 Japan. It is maintained at Shiga-ken Moryama-shi, 1465 Sugie-cho, Japan and parent stock is maintained by soil cultivation. The variety is primarily used as a potted plant and for cut flowers. Planting in Japan is from mid-October to late December. Grafting is from late September to early October. The plant will flower annually when grown in a greenhouse.

BRIEF DESCRIPTION OF THE PHOTOGRAPHS

The accompanying photographs illustrate the appearance of the new *Rosa* L. variety. The colors in the photographs are depicted as nearly true as is reasonably possible to obtain in colored reproductions of this type. Colors as shown in the photographs may differ slightly from the color values cited in the detailed botanical description.

Figure 2:
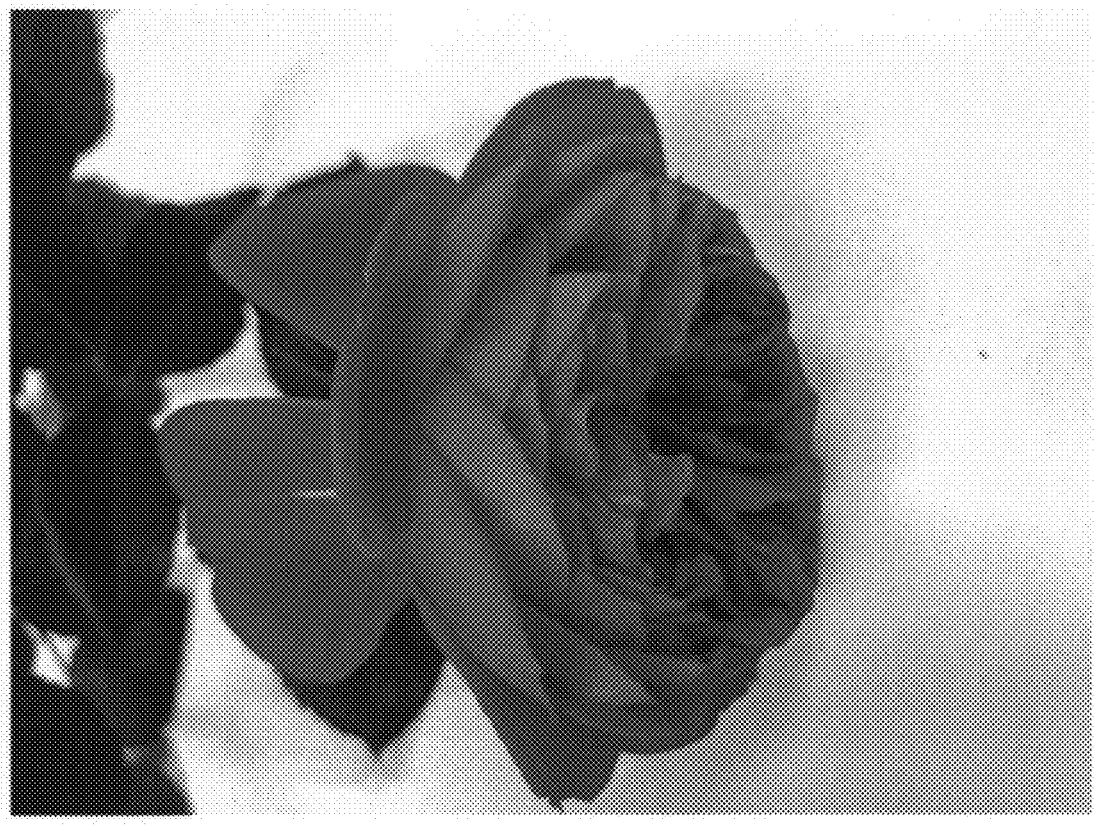
Figure 3:
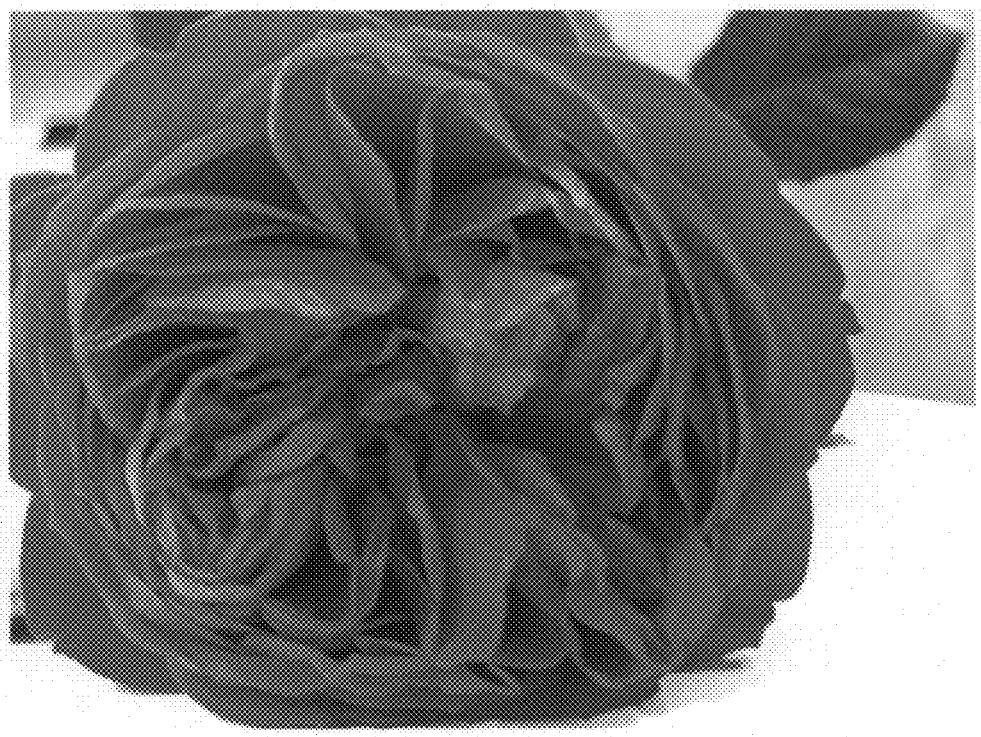
Figure 4:
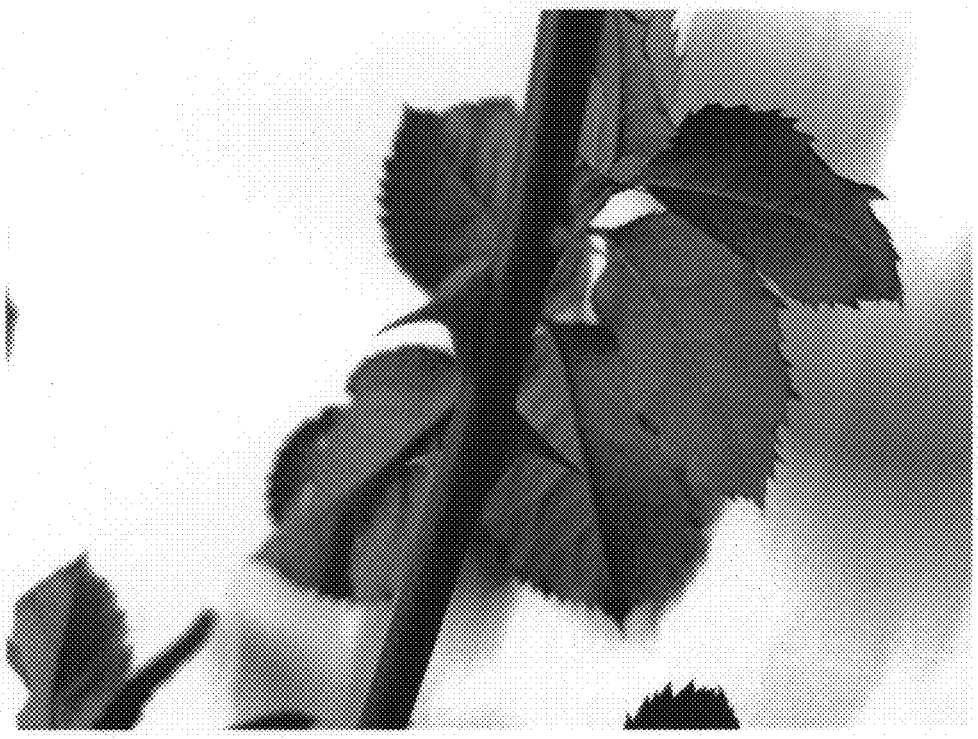
Figure 5:
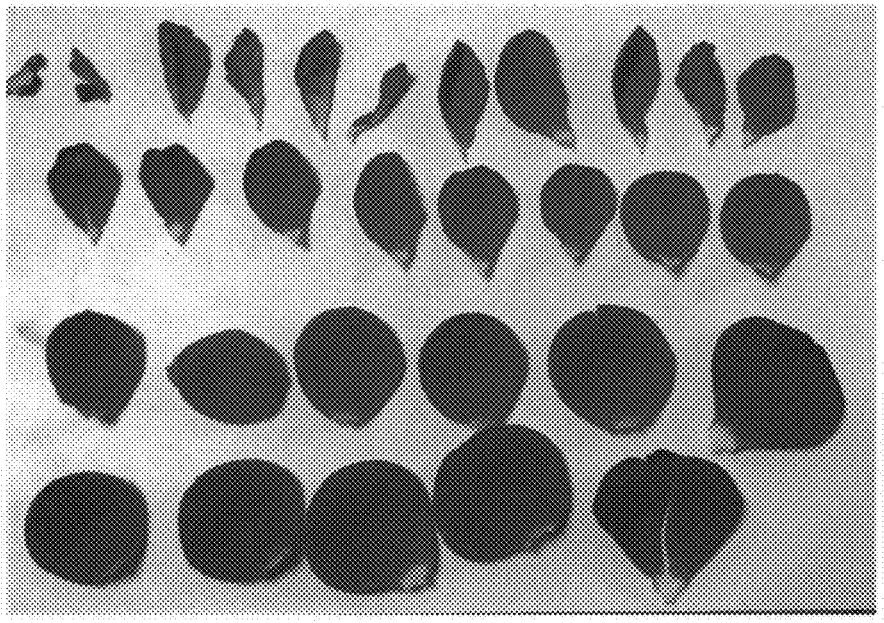

FIG. 1 shows a branch with a flower and leaves.
FIG. 2 shows a close-up side view of a flower.
FIG. 3 shows a close-up front view of a flower.
FIG. 4 shows the prickles on a branch.
FIG. 5 shows individual petals.

Figure 6:
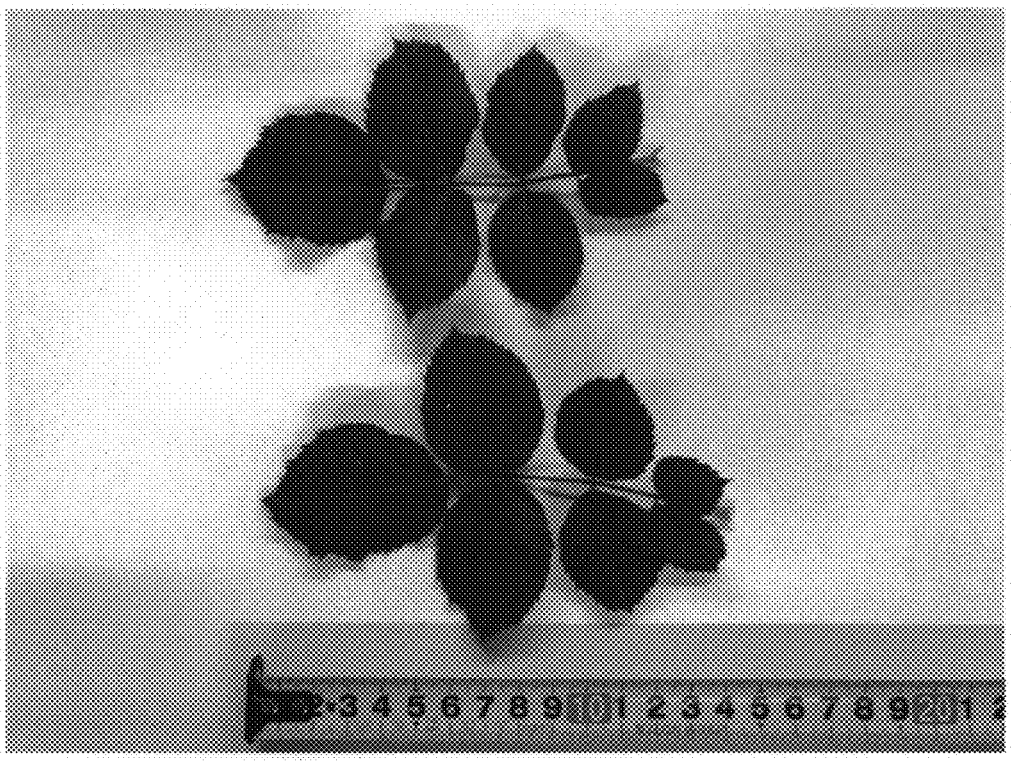
Figure 7:
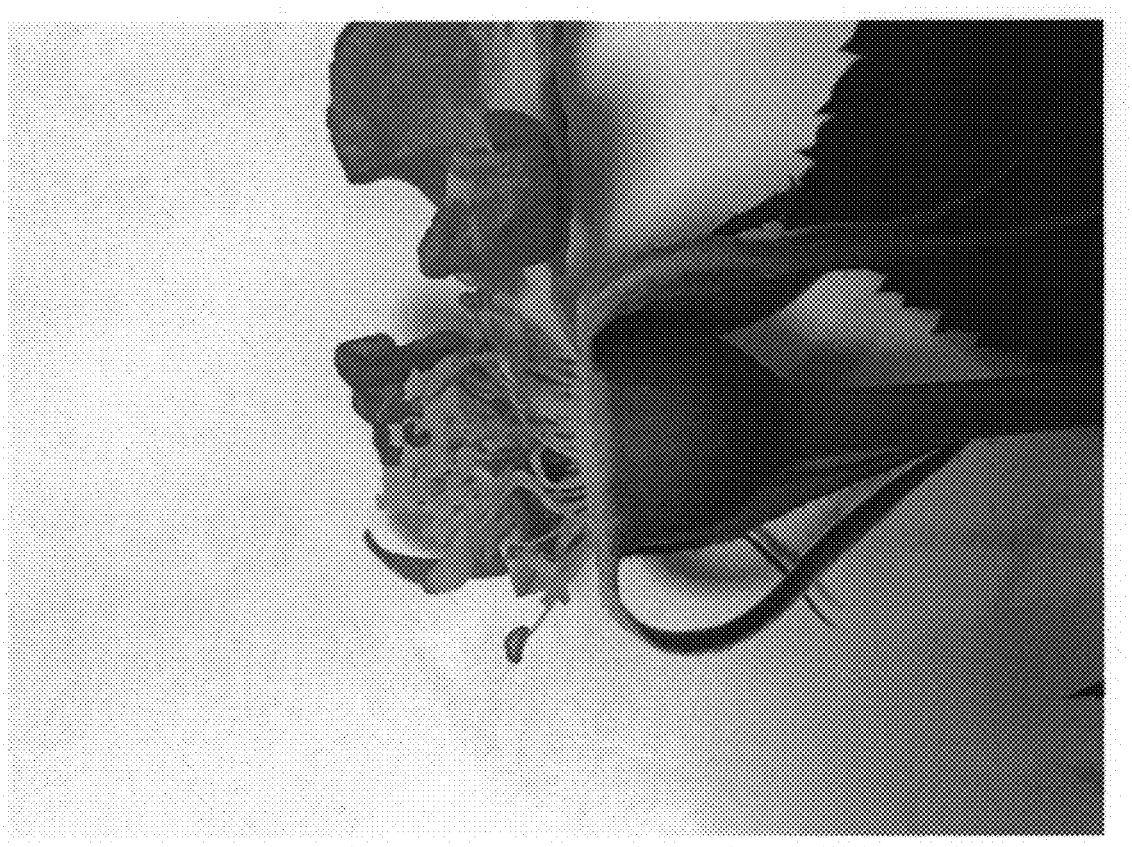

FIG. 6 shows leaves with leaflets.
FIG. 7 shows reproductive organs of a flower.

DETAILED BOTANICAL DESCRIPTION

The following is a detailed description of '80102WABARA' with color descriptions based on The Royal Horticultural Society (R.H.S.) Colour Chart for those colors referred to by R.H.S. designation.

CHARACTERISTICS OF VARIETY

Plant:
- *Growth type*.—Shrub.
- *Growth habit*.—Semi-upright.
- *Height*.—71 cm.
- *Young shoot, anthocyanin coloration*.—Present.
- *Stem size*.—About 0.6 cm.
- *Stem, number of prickles* (*excluding hair-like prickles*) .—Few.
- *Prickle size*.—About 0.8 cm.
- *Prickles, predominant color*.—RHS 177B.
- *Bark color*.—RHS 137B.

Leaf:
- *Size*.—13 cm.
- *Width of leaf*.—About 4.0 cm.
- *Color*.—RHS 147A.
- *Anthocyanin coloration*.—Present.
- *Glossiness of upper side*.—Weakly glossy.
- *Leaflet, undulation of margin*.—Very weak.
- *Leaflet color*.—RHS 147A.
- *Terminal leaflet, blade shape*.—Ovate.
- *Terminal leaflet shape of base of blade*.—Rounded.
- *Terminal leaflet shape of apex of blade*.—Acuminate.
- *Terminal leaflet size*.—About 4.5 cm.
- *Terminal leaflet color*.—RHS 147A (upper surface), RHS 139C (lower surface).

Flowers:
- *Flowering shoot, flowering laterals*.—Present.
- *Flowering shoot, number of flowering laterals*.—1 lateral.
- *Flowering shoot, number of flowers*.—1 flower.
- *Flowering shoot number of flowers per lateral*.—1 flower.
- *Flower type*.—Double.
- *Number of petals*.—115.
- *Flower color group*.—Reddish.
- *Density of petals* (*for double flowered variety*).—Medium (on a scale of very loose, loose, medium, or dense).
- *Flower diameter*.—9 cm.
- *Flower shape*.—Flattened convex.
- *Profile of upper part of flower*.—Flat.
- *Profile of lower part of flower*.—Flat.
- *Fragrance*.—Strong.
- *Sepal, extensions*.—Weak.
- *Reflexing of petals one-by-one*.—Absent.
- *Petal shape*.—Changes from elliptic to fan-shaped from the center part to the outside.
- *Petal incisions*.—Very weak.
- *Reflexing of petal margin*.—Medium, center part is strong.
- *Petal undulation*.—Weak, center part is medium.
- *Petal length*.—3.5 cm.
- *Petal width*.—4.5 cm.
- *Number of colors on inner side of petal*.—Two.
- *Intensity of petal color*.—Lighter towards the top.
- *Main color on inner side of petal*.—Darker than RHS N57A.
- *Secondary color of petal*.—RHS N66.
- *Distribution of secondary color on inner side of petal*.—At apex.
- *Basal spot on the inner side of petal*.—Present.
- *Size of basal spot on inner side*.—Small.
- *Color of petal of basal spot on inner side of petal*.—Medium yellow.
- *Main color of petal on the outer side*.—RHS 61B.
- *Distribution of color of petals*.—Middle zone (middle part) 90%, Spot at the base: 10%.
- *Outer stamen, predominant color of filament*.—Light yellow.

What is claimed is:

1. A new and distinct variety of a *Rosa* L. rose plant having the characteristics substantially as described and illustrated herein.

* * * * *